US006713579B2

(12) United States Patent
Sonnenschein et al.

(10) Patent No.: US 6,713,579 B2
(45) Date of Patent: Mar. 30, 2004

(54) AMINE ORGANOBORANE COMPLEX POLYMERIZATION INITIATORS AND POLYMERIZABLE COMPOSITIONS

(75) Inventors: Mark F. Sonnenschein, Midland, MI (US); Steven P. Webb, Midland, MI (US); Nelson G. Rondan, Missouri City, TX (US)

(73) Assignee: Dow Global Technologies Inc., Midland, MI (US)

( * ) Notice: Subject to any disclaimer, the term of this patent is extended or adjusted under 35 U.S.C. 154(b) by 144 days.

(21) Appl. No.: 09/882,510

(22) Filed: Jun. 15, 2001

(65) Prior Publication Data

US 2002/0031607 A1 Mar. 14, 2002

Related U.S. Application Data

(63) Continuation-in-part of application No. 09/466,321, filed on Dec. 17, 1999.

(51) Int. Cl.[7] .............................. C08F 4/52; C08F 4/44; B01J 31/00; C07F 5/02; B32B 7/12
(52) U.S. Cl. ..................... 526/196; 526/134; 502/162; 502/170; 502/200; 502/202; 564/1; 564/8; 564/9; 428/355
(58) Field of Search ............................. 526/196, 134; 502/200, 202, 162, 170; 564/1, 8, 9; 428/355

(56) References Cited

U.S. PATENT DOCUMENTS

| | | | |
|---|---|---|---|
| 3,275,611 A | 9/1966 | Mottus et al. ............. 260/80.5 |
| 3,527,737 A | 9/1970 | Masuhara et al. ......... 260/78.5 |
| 4,385,153 A | 5/1983 | Ritter ........................ 524/522 |
| 4,515,724 A | 5/1985 | Ritter ........................ 260/410 |
| 4,676,858 A | 6/1987 | Ritter ........................ 156/307 |
| 4,920,188 A | 4/1990 | Sakashita ................... 526/196 |
| 4,921,921 A | 5/1990 | Ritter ........................ 526/195 |
| 4,985,516 A | 1/1991 | Sakashita et al. .......... 526/196 |
| 5,034,464 A | 7/1991 | Arduengo ................... 525/207 |
| 5,106,928 A | 4/1992 | Skoultchi et al. .......... 526/196 |
| 5,143,884 A | 9/1992 | Skoultchi et al. .......... 502/160 |
| 5,286,821 A | 2/1994 | Skoultchi et al. .......... 526/196 |
| 5,310,835 A | 5/1994 | Skoultchi et al. .......... 526/198 |
| 5,376,746 A | 12/1994 | Skoultchi et al. .......... 526/196 |
| 5,401,805 A | 3/1995 | Chung et al. .............. 525/288 |
| 5,539,070 A | 7/1996 | Zharov et al. ............. 526/198 |
| 5,616,796 A | 4/1997 | Pocius et al. .............. 564/569 |
| 5,621,143 A | 4/1997 | Pocius ....................... 564/568 |
| 5,681,910 A | 10/1997 | Pocius ....................... 526/198 |
| 5,684,102 A | 11/1997 | Pocius et al. .............. 526/198 |
| 5,686,544 A | 11/1997 | Pocius ....................... 526/196 |
| 5,690,780 A | 11/1997 | Zharov ...................... 156/332 |
| 5,691,065 A | 11/1997 | Zharov ...................... 428/421 |
| 5,718,977 A | 2/1998 | Pocius ....................... 428/422 |
| 5,795,657 A | 8/1998 | Pocius et al. .............. 428/516 |
| 5,872,197 A | 2/1999 | Deviny ...................... 526/196 |
| 5,883,208 A | 3/1999 | Deviny ...................... 526/198 |
| 5,912,433 A | 6/1999 | Pulido ....................... 174/77 |
| 5,935,711 A | 8/1999 | Pocius et al. .............. 428/421 |
| 5,952,409 A | 9/1999 | Boardman et al. ......... 524/185 |
| 5,990,036 A | 11/1999 | Deviny ...................... 502/162 |
| 5,994,484 A | 11/1999 | Pocius ....................... 526/196 |
| 6,008,308 A | 12/1999 | Pocius ....................... 526/196 |
| 6,027,813 A | 2/2000 | Deviny ...................... 428/422 |
| 6,093,778 A | 7/2000 | Pocius ....................... 526/196 |
| 6,252,023 B1 | 6/2001 | Moren ....................... 526/196 |
| 6,410,667 B1 * | 6/2002 | Moren ....................... 526/217 |

FOREIGN PATENT DOCUMENTS

| | | |
|---|---|---|
| WO | 97/07171 | 2/1997 |
| WO | 98/17694 | 4/1998 |

OTHER PUBLICATIONS

Chemical Abstracts, vol. 119, 1983, p. 78, 119:74163c Acrylic Adhesive Composition and Organoborane Initiator System.
Derwent Abstract, 96–453820/45, ADGE=93.05.28, Adgeziv Co. Ltd., RU 2054022–C1, 1993.
Polymer Letters, vol. 8, pp. 541–547 (1970) Polymerization of Methyl Methacrylate by Trialkylborane–Pyridine System.
Love, Peter et al., "Polar Substituent Effects in Gas–Phase Lewis Acid–Base Equilibria. I. Intrinsic Basicity of Amines", J. Amer. Chem. Soc. (1968), 90(10), 2455–62 XP000982168, tables, I, EX.5 columns 4 and 5.
Chemical Abstracts, Fujisawa, Seiichiro et al., "Dental Self–Curing Resins. XI. Characterization of Several Complexes of tri–n–butyl Borane as an Initiator" 73:88532, XP002160417–Abstract & Iyo Kizai Kenkyusho Hokoku, Tokyo Ika Shika Daigaku (1969), 3, 64–71.
Koester, Roland et al., "Boron compounds. XXVII. Borylation of several amino carboxylic acids", Justus Liebigs Ann, Chem. (1974), (1), 112–19 XP000982170, (no translation provided).
Journal of Organometallic Chemistry, , Hoberg et al., 1976, 118(1), C3–C5 (no translation provided).
ZH. Obshch. Khim., Dorokhov et al., 1976, 46(5), pp. 1053–1059.

* cited by examiner

Primary Examiner—Richard L. Raymond
Assistant Examiner—Tamthom N. Truong
(74) Attorney, Agent, or Firm—Norman L. Sims

(57) ABSTRACT

A method of modifying the surface of a low surface energy polymer by contacting the surface with a composition comprising a) an organoborane/amine complex wherein the amine is selected from the group of amines having an amidine structural component; aliphatic heterocycles having at least one nitrogen in the heterocyclic ring; an alicyclic compound having bound to the ring a substituent having an amine moiety; amines which in addition to a primary amine have one or more hydrogen bond accepting groups of an ether, polyether, thioether or halogen wherein there is an alkylene chain of at least two carbon atoms between the primary amine and the hydrogen bond accepting group, and conjugated imines; b) one or more of monomers, oligomers or polymers having olefinic unsaturation; and optionally, c) an effective amount of a compound which causes the complex to disassociate.

19 Claims, No Drawings

AMINE ORGANOBORANE COMPLEX POLYMERIZATION INITIATORS AND POLYMERIZABLE COMPOSITIONS

CROSS REFERENCE TO RELATED APPLICATION

This application is a continuation-in-part (CIP) of copending application Ser. No. 09/466,321, filed Dec. 17, 1999.

BACKGROUND OF THE INVENTION

This invention relates to organoborane amine complexes that are useful as free radical polymerization initiators. In another embodiment, this invention relates to polymerizable compositions comprising compounds containing moieties capable of free radical polymerization and organoborane amine complex initiators of the invention. In yet another embodiment the invention relates to adhesive, sealant, coating and ink compositions containing organoborane amine complexes and compounds containing moieties capable of free radical polymerization.

In many practical situations in which compounds are subjected to polymerization or where adhesives are used, it is desirable to have polymerizable compositions and adhesive compositions which can cure on demand. Cure on demand means that the polymerization can be initiated when desired. A significant problem with cure on demand compositions is the stability of the compositions. Many such compositions will begin curing at, or near, ambient temperature or will partially cure at ambient temperature resulting in an increased viscosity causing difficulties in handling and reduced functionality of the polymerizable composition or adhesive composition.

Low surface energy olefins such as polyethylene, polypropylene and polytetrafluroethylene have a variety of attractive properties in a variety of uses, such as for toys, automobile parts, furniture applications and the like. Because of the low surface energy of these plastic materials, it is very difficult to find adhesive compositions which bond to these materials. The commercially available adhesives which are used for these plastics require time consuming or extensive pretreatment of the surface before the adhesive will bond to the surface. Such pretreatments include corona treatment, flame treatment and the like. The requirement for extensive pretreatment of the surface results in significant limitations to the designers of automobile components, toys, furniture and the like. What is needed is adhesive compositions which are capable of bonding to low surface energy substrates, and bonding low surface energy substrates to other substrates, without the need for extensive or costly pretreatment.

Mottus et al., U.S. Pat. No. 3,275,611 discloses a process for polymerizing olefinic compounds with a catalyst comprising an organoborane compound, a peroxygen compound and an amine (incorporated herein by reference). It is disclosed that the organoborane compound and amine may be added to the reaction mixture separately or as a preformed complex, and that the complex is preferred. The presence of the amine in the complex reduces the pyrophoricity of the organoborane in air. Among the amine complexing agents disclosed are pyridine, aniline, toluidine, dimethylbenzylamine, and nicotine. Many of the complexes disclosed in Mottus are pyrophoric at all amine to boron atom ratios. In addition, many of the amine complexes do not display significant adhesive properties when applied to low surface energy substrates.

A series of patents issued to Skoultchi (U.S. Pat. Nos. 5,106,928, 5,143,884, 5,286,821, 5,310,835 and 5,376,746) (all incorporated herein by reference) disclose a two-part initiator system that is reportedly useful in acrylic adhesive compositions. The first part of the two-part system includes a stable organoborane-amine complex and the second part includes a destabilizer or activator such as an organic acid or an aldehyde. The organoborane compound of the complex has three ligands which can be selected from $C_{1-10}$ alkyl groups or phenyl groups. Useful amines disclosed include octylamine, 1,6 diaminohexane, diethylamine, dibutylamine, diethylenetriamine, dipropylenediamine, 1,3 propylene diamine, and 1,2 propylene diamine. The adhesive compositions are disclosed to be useful in structural and semi-structural adhesive applications, such as speaker magnets, metal to metal bonding, automotive glass to metal bonding, glass to glass bonding, circuit board component bonding, bonding select plastics to metal, glass to wood, etc. and for electric motor magnets.

Zharov et al. discloses in a series of US Patents (U.S. Pat. Nos. 5,539,070; 5,690,780; and 5,691,065) (all incorporated herein by reference) polymerizable acrylic compositions which are particularly useful as adhesives wherein organoborane amine complexes are used to initiate cure. The organoboranes used have three ligands attached to the borane atom which are selected from $C_{1-10}$ alkyl groups and phenyl. The amine is an alkanol amine or a diamine where the first amine group can be a primary or secondary amine and the second amine is a primary amine. It is disclosed that these complexes are good for initiating polymerization of an adhesive which bonds to low surface energy substrates.

Pocius in a series of patents (U.S. Pat. Nos. 5,616,796; 5,6211,43; 5,681,910; 5,686,544; 5,718,977; and 5,795,657) (all incorporated herein by reference) disclose amine organoborane complexes with a variety of amines such as polyoxyalkylene polyamines and polyamines which are the reaction product of diprimary amines and compound having at least two groups which react with a primary amine.

Many of the complexes disclosed in the Zharov, Skoultchi and Pocius Patents are not stable in compositions containing olefinic unsaturation at, or near, ambient temperatures and thus the complexes disassociate and induce polymerization at, or near, ambient temperature with time. This instability at, or near, ambient temperature can result in polymerization before desired and can result in compositions which are unsuitable for the desired use.

Therefore, there is a need for initiator systems for free radical polymerization which are safe to handle, not pyrophoric, which can be used to form cure on demand polymer systems or can be used in adhesive systems which cure on demand. What is further needed are adhesive systems which are capable of bonding to low surface energy substrates, and initiator systems which facilitate such bonding. In addition to such needs, the complexes need to be thermally stable, that is do not disassociate at, or near, ambient temperatures and thereby initiate polymerization before desired. What are further needed are polymer compositions and adhesive systems which are thermally stable at, or near, ambient temperatures and which will undergo polymerization when the user desires.

SUMMARY OF INVENTION

In one embodiment the invention is an amine organoborane complex wherein the organoborane is a trialkyl borane and the amine is selected from the group of amines having an amidine structural component; aliphatic heterocycles having at least one nitrogen in the heterocyclic ring wherein the heterocyclic compound may also contain one or more nitrogen atoms, oxygen atoms, sulfur atoms, or double bonds in the heterocycle; an alicyclic compound having bound to the ring a substituent having an amine moiety wherein the compound may have a second substituent which can contain one or more nitrogen, oxygen, sulfur or one or two double bonds; primary amines which in addition have one or more hydrogen bond accepting groups wherein there are at least two carbon atoms, preferably at least three carbon atoms, between the primary amine and the hydrogen bond accepting group, such that due to inter- or intramolecular interactions within the complex the strength of the B—N bond is increased; and conjugated imines. Preferred hydrogen bond accepting groups include the following: primary amines, secondary amines, tertiary amines, ethers, halogens, polyethers or polyamines. Heterocycle as used herein refers to a compound having one or more aliphatic cyclic rings of which one of the rings contains nitrogen. The amidines or conjugated imines can be straight or branched chain or cyclic.

In another embodiment the invention comprises a polymerizable composition which comprises an amine organoborane complex of the invention and one or more of monomers, oligomers or polymers having olefinic unsaturation which are capable of polymerization by free radical polymerization. This composition can undergo polymerization by exposing the composition to temperatures at which the organoborane amine complex undergoes disassociation. In another embodiment the invention is a polymerizable composition which further comprises an effective amount of a compound which causes the complex to disassociate (decomplexing agent), thereby freeing the borane to initiate polymerization of the one or more monomers, oligomers or polymers having olefinic unsaturation. The compound which causes disassociation of the complex is kept separate from the complex until initiation of polymerization is desired. In yet another embodiment the invention is a method of polymerization comprising a contacting of the components of the polymerizable compositions under conditions that the one or more monomers, oligomers or polymers undergo polymerization. The polymerizable composition which contains the decomplexing agent can be cured at any desired temperature, such as at, or near, ambient temperature and below ambient temperature.

The polymerizable compositions of the invention can be used as adhesive, sealant, coating or ink compositions. In one embodiment two or more substrates are bonded together by contacting the components of the adhesive composition of the invention, including the decomplexing agent, together under conditions such that polymerization is initiated; contacting the adhesive composition with the two or more substrates; positioning the two or more substrates such that the adhesive composition is located between the two or more substrates wherein they are in contact with one another; and allowing the adhesive to cure so as to bond the two or more substrates together. The thermally curing compositions of the invention can be used to bond two or more substrates together by contacting the adhesive composition with the substrates such that the adhesive composition is located between the two or more substrates and exposing the adhesive composition to a temperature at which the complex disassociates and initiating the free radical polymerization of the monomer, oligomers, polymers or a mixture thereof.

The complexes of the invention are safe to handle, not pyrophoric, are stable at, or near, ambient temperature and therefore will not initiate polymerization at, or near, ambient temperature in the absence of an initiator that causes the complex to disassociate. The polymeric compositions of the invention are stable at, or near, ambient temperature and can be cured upon demand by contacting the complex with the compounds which cause disassociation of the complex, or alternatively by heating the polymeric compositions above the thermal disassociation temperature of the complex. Furthermore, the adhesive, sealant, coating and ink compositions of the invention can form good bonds to low surface energy substrates without the need for primers or surface treatment.

DETAILED DESCRIPTION OF THE INVENTION

The organoborane used in the complex is a trialkyl borane or an alkyl cycloalkyl borane. Preferably such borane corresponds to Formula 1:

$$B-(R^2)_3 \qquad \text{Formula 1}$$

wherein B represents Boron; and $R^2$ is separately in each occurrence a $C_{1-10}$ alkyl, $C_{3-10}$ cycloalkyl, or two or more of $R^2$ may combine to form a cycloaliphatic ring. Preferably $R^2$ is $C_{1-4}$ alkyl, even more preferably $C_{2-4}$ alkyl, and most preferably $C_{3-4}$ alkyl. Among preferred organoboranes are tri-ethyl borane, tri-isopropyl borane and tri-n-butylborane. To prepare thermally stable polymerizable compositions, thermally stable complexes which do not disassociate, at or near, ambient temperature are needed. The key to preparation of such complexes, is the selection of the amine. The desirability of the use of a given amine in an amine/organoborane complex can be calculated from the energy difference between the Lewis acid-base complex and the sum of energies of the isolated Lewis acid (organoborane) and base (amine) known as binding energy. The higher the binding energy the more stable the complex.

Binding Energy=(Complex Energy−(Energy of Lewis Acid+ Energy of Lewis base))

Such binding energies can be calculated using theoretical ab-initio methods such as the Hartree Fock method and the 3-21G basis set. These computational methods are available commercially employing commercial software and hardware such as SPARTAN and GAUSSIAN 98 programs with a Silicon Graphics workstation. Amines having amine/organoborane binding energies of ten kilocalories per mol or greater are preferred, amines having a binding energy of 15 kilocalories per mol or greater are more preferred and even more preferred are amines with a binding 20 kilocalories per mol or greater. In the embodiment where polymerization of the compositions of the invention is initiated by use of a decomplexing agent the binding energy of the amine to the organoborane is preferably about 50 kcal/mole or less and most preferably about 30 kcal/mole or less. In the embodiment where polymerization of the compositions of the invention is initiated by use of heat the binding energy of the amine is preferably about 100 kcal/mole or less, more preferably about 80 kcal/mole or less and most preferably about 50 kcal/mole or less.

In one embodiment, the amine comprises a compound having a primary amine and one or more hydrogen bond accepting groups, wherein there are at least two carbon atoms, preferably at least about three, between the primary amine and hydrogen bond accepting groups. Preferably an alkylene moiety is located between the primary amine and the hydrogen accepting group. Hydrogen bond accepting group means herein a functional group that through either inter- or intramolecular interaction with a hydrogen of the borane-complexing amine increases the electron density of the nitrogen of the amine group complexing with the borane.

Preferred hydrogen bond accepting groups include primary amines, secondary amines, tertiary amines, ethers, halogen, polyethers, thioethers, and polyamines. More preferred hydrogen accepting groups are ethers, polyethers, thioethers and halogens. In a preferred embodiment, the amine corresponds to Formula 2:

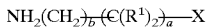  Formula 2 wherein:
$R^1$ is separately in each occurrence hydrogen a $C_{1-10}$ alkyl, $C_{3-10}$ cycloalkyl;
X is hydrogen bond accepting moiety; a is an integer of about 1 to about 10; and b is separately in each occurrence an integer of about 0 to about 1, and the sum of a and b is from about 2 to about 10. Preferably $R^1$ is hydrogen or methyl. Preferably X is separately in each occurrence a hydrogen accepting moiety with the proviso that when the hydrogen accepting moiety is an amine it is a tertiary or a secondary amine. More preferably X is separately in each occurrence —$N(R^8)_e$, —$OR^{10}$, $SR^{10}$ or a halogen wherein $R^8$ is separately in each occurrence $C_{1-10}$ alkyl, $C_{3-10}$ cycloalkyl or —$(C(R^1)_2)_d$—W; $R^{10}$ is separately in each occurrence, $C_{1-10}$ alkyl, $C_{3-10}$ cycloalkyl, or —$(C(R^1)_2)_d$—W; and e is 0, 1, or 2. More preferably X is $SR^{10}$, —$OR^{10}$ or halogen. Most preferably X is $SR^{10}$ or $OR^{10}$. Preferably, $R^8$ and $R^{10}$ are $C_{1-4}$ alkyl or —$(C(R^1)_2)_d$—W, more preferably $C_{1-4}$ alkyl and most preferably methyl. W is separately in each occurrence hydrogen or $C_{1-10}$ alkyl or X and more preferably hydrogen or $C_{1-4}$ alkyl. Preferably, a is about 1 or greater and more preferably 2 or greater. Preferably a is about 6 or less, and most preferably about 4 or less. Preferably, b is about 1. Preferably, the sum of a and b is an integer about 2 or greater and most preferably about 3 or greater. Preferably the sum of a and b are about 6 or less and more preferably about 4 or less. Preferably d is separately in each occurrence an integer of about 1 to about 4, more preferably about 2 to about 4, and most preferably about 2 to about 3. Among preferred amines corresponding to Formula 2 are dimethylaminopropyl amine, methoxypropyl amine, dimethylaminoethylamine, dimethylaminobutylamine, methoxybutyl amine, methoxyethyl amine, ethoxypropylamine, propoxypropylamine, amine terminated polyalkylene ethers (such as trimethylolpropane tris(poly(propyleneglycol), amine terminated)ether), and aminopropylpropanediamine.

In one embodiment the preferred amine complex corresponds to Formula 3:

  Formula 3 wherein $R^1$, $R^2$, X, a and b are as defined hereinbefore.

In another embodiment the amine is an aliphatic heterocycle having at least one nitrogen in the heterocycle. The heterocyclic compound may also contain one or more of nitrogen, oxygen, sulfur or double bonds. In addition, the heterocycle may comprise multiple rings wherein at least one of the rings has a nitrogen in the ring. Preferably the aliphatic heterocyclic amine corresponds to Formula 4:

Formula 4

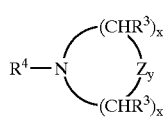

wherein:
$R^3$ is separately in each occurrence hydrogen, a $C_{1-10}$ alkyl $C_{3-10}$ cycloalkyl or forms a double bond with a $R^3$ or $R^4$ on an adjacent atom;
Z is separately in each occurrence oxygen, sulfur or $NR^4$ wherein $R^4$ is hydrogen, $C_{1-10}$ alkyl, or $C_{6-10}$ aryl or alkaryl;
x is separately in each occurrence an integer of about 1 to about 10, with the proviso that the total of all occurrences of x should be from about 2 to about 10; and
y is separately in each occurrence 0 or 1. Two or more of $R^3$ and $R^4$ may combine to form cyclic rings thereby forming a multicyclic compound. Preferably, $R^3$ is separately in each occurrence hydrogen, methyl or forms a double bond with a $R^3$ or $R^4$ on an adjacent atom. Preferably Z is $NR^4$. Preferably, $R^4$ is hydrogen or $C_{1-4}$ alkyl, and more preferably hydrogen or methyl. Preferably x is from about 1 to about 5 and the total of all the occurrences of x is about 3 to about 5. Preferred compounds corresponding to Formula 4 include morpholine, piperidine, pyrolidine, piperazine, 1,3,3 trimethyl 6-azabicyclo[3,2,1] octane, thiazolidine, homopiperazine, aziridine, 1,4-diazabicylo [2.2.2]octane (DABCO), 1-amino-4-methylpiperazine, 3-pyrroline, aminopropylmorpholine, and the like. Complexes containing aliphatic heterocyclic amines preferably correspond to Formula 5:

Formula 5

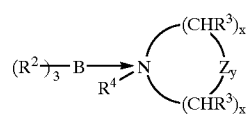

wherein $R^2$, $R^3$, Z, x and y are as defined hereinbefore.

In yet another embodiment, the amine which is complexed with the organoborane is an amidine. Any compound with amidine structure wherein the amidine has sufficient binding energy as described hereinbefore with the organoborane, may be used. Preferable amidine compounds correspond to Formula 6:

Formula 6

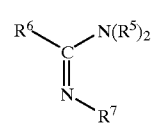

wherein:
$R^5$ and $R^6$ and are separately in each occurrence hydrogen, a $C_{1-10}$ alkyl, $C_{3-10}$ cycloalkyl or $N(R^4)_2$; two or more of $R^5$, $R^6$, and $R^7$ may combine in any combination to form a ring structure, which may have one or more rings. Preferably $R^5$ and $R^6$ are separately in each occurrence hydrogen, $C_{1-4}$ alkyl or $C_{5-6}$ cycloalkyl or $N(R^4)_2$. Preferably $R^7$ is separately in each occurrence hydrogen, $C_{1-10}$ alkyl, $C_{3-10}$ cycloalkyl or part of a ring structure. Most preferably $R^7$ is H, methyl or part of a cyclic ring. In the embodiment where two or more of $R^5$, $R^6$ and $R^7$ combine to form a ring structure the ring structure is preferably a single or a double ring structure. Among preferred amidines are 1,8 diazabicyclo[5,4]undec-7-ene; tetrahydropyrimidine; 2-methyl-2-imidazoline; and 1,1,3,3-tetramethylguanidine, and the like.

The organoborane amidine complexes preferably correspond to Formula 7:

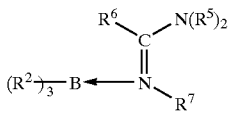

Formula 7 wherein $R^2$, $R^5$, $R^6$ and $R^7$ are as defined earlier.

In yet another embodiment, the amine which is complexed with the organoborane is a conjugated imine. Any compound with a conjugated imine structure, wherein the imine has sufficient binding energy as described hereinbefore with the organoborane, may be used. The conjugated imine can be a straight or branched chain imine or a cylic imine. Preferable imine compounds correspond to Formula 8:

$$NR^7=CR^9-(CR^9=CR^9)_c-Y$$  Formula 8 wherein Y is independently in each occurrence hydrogen, $SR^4$, $N(R^4)_2$, $OR^4$, $C(O)OR^4$, halogen or an alkylene group which forms a cyclic ring with an $R^7$ or $R^9$. $R^4$ is hydrogen, $C_{1-10}$ alkyl, $C_{6-10}$ aryl or $C_{6-10}$ alkaryl. Preferably $R^4$ is hydrogen or methyl. $R^7$ is as described previously. $R^9$ is independently in each occurrence hydrogen, Y, $C_{1-10}$ alkyl, $C_{3-10}$ cycloalkyl-, $-(C(R^{9'})_2-(CR^{9'}=CR^{9'})_c-)Y$ or two or more of $R^9$ can combine to form a ring structure provided the ring structure is conjugated with respect to the double bond of the imine nitrogen; and c is an integer of from about 1 to about 10. Preferably, $R^9$ is hydrogen, $C_{1-10}$ alkyl, Y or $-(C(R^{9'})_2-(CR^{9'}=CR^{9'})_c-)Y$; and most preferably, $R^9$ is hydrogen or methyl. Y is preferably $SR^4$, $N(R^4)_2$, or $OR^4$, or an alkylene group which forms a cyclic ring with $R^7$ or $R^9$. Y is more preferably $N(R^4)_2$ or an alkylene group which forms a cyclic ring with $R^7$ or $R^9$. Preferably, c is an integer of from about 1 to about 5, and most preferably about 1. Among preferred conjugated imines useful in this invention are 4-dimethylaminopyridine; 2,3-bis(dimethylamino) cyclopropeneimine; 3-(dimethylamine)acroleinimine; 3-(dimethylamino)methacroleinimine, and the like.

$R^{9'}$is independently in each occurrence hydrogen, $C_{1-10}$ alkyl, $C_{3-10}$ cycloalkyl or Y and most preferably hydrogen or methyl.

Among preferred cyclic imines are those corresponding to the following structures

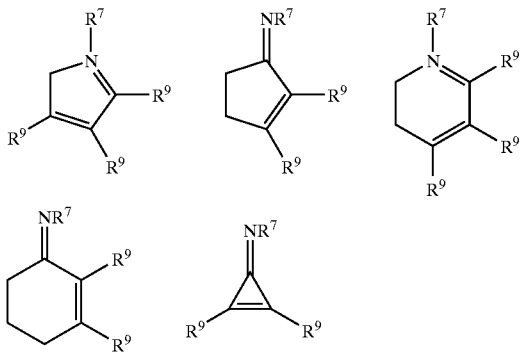

The complexes with the conjugated imines preferably correspond to Formula 9:

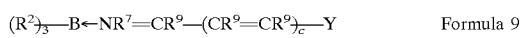

$$(R^2)_3-B \leftarrow NR^7=CR^9-(CR^9=CR^9)_c-Y$$  Formula 9 wherein $R^2$, $R^7$, $R^9$, c and Y are as defined hereinbefore.

In another embodiment the amine can be an alicyclic compound having bound to the alicyclic ring a substituent containing an amine moiety. The amine containing alicyclic compound may have a second substituent which contains one or more nitrogen, oxygen or sulfur atoms or a double bond. The alicyclic ring can contain one or two double bonds. The alicyclic compound may be a single or multiple ring structure. Preferably the amine on the first substituent is primary or secondary. Preferably the alicyclic ring is a 5 or 6 membered ring. Preferably functional groups on the second substituent are amines, ethers, thioethers, halogens. Preferably the amines are secondary or tertiary. In a preferred embodiment the alicyclic compound with an amine containing substituent corresponds to Formula 10

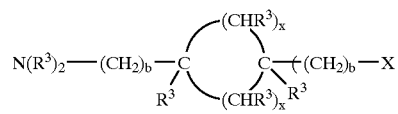

wherein $R^3$, X, and x are as described hereinbefore. Included in amine substituted alicyclic compounds is isophorone diamine. B is amino methyl cyclohexane in all its isomeric forms.

Complexes using amine substituted alicyclic compounds correspond to Formula 11

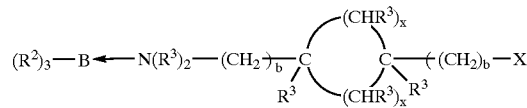

wherein $R^2$, $R^3$, X, a, b and x are as defined hereinbefore.

The molar ratio of amine compound to borane compound in the complex is relatively important. In some complexes if the molar ratio of amine compound to organoborane compound is too low, the complex is pyrophoric. Preferably the molar ratio of amine compound to organoborane compound is from about 1.0:1.0 to about 3.0:1.0. Below the ratio of about 1.0:1.0 there may be problems with polymerization, stability of the complex and for adhesive uses, adhesion. Greater than about a 3.0:1.0 ratio may be used although there is no benefit from using a ratio greater than about 3.0:1.0. If too much amine is present, this may negatively impact the stability of the adhesive or polymer compositions. Preferably the molar ratio of amine compound to organoborane compound is from about 2.0:1.0 to about 1.0:1.0.

Polymerizable compounds which may be used in the polymerization compositions of the invention include any monomers, oligomers, polymers or mixtures thereof which contain olefinic unsaturation which can polymerize by free radical polymerization. Such compounds are well known to those skilled in the art. Mottus, U.S. Pat. No. 3,275,611, provides a description of such compounds at column 2, line 46 to column 4, line 16, incorporated herein by reference. Among preferred classes of compounds containing olefinic unsaturation are monomers, oligomers, polymers and mixtures thereof derived from the acrylates and methacrylates; olefinically unsaturated hydrocarbons, for example ethylene, propylene, butylene, isobutylene, 1-octene, 1-dodecene, 1-heptadecene, 1-eicosene and the like; vinyl compounds such as styrene, vinyl pyridine, 5-methyl-2 vinylpyridine, vinyl napthylene, alpha methylstyrene; vinyl and vinylidiene halides; acrylonitrile and methacrylonitrile; vinyl acetate and vinyl propionate; vinyl oxyethanol; vinyl trimethylacetate; vinyl hexonate; vinyl laurate; vinyl chloroacetate;

vinyl stearate; methyl vinyl ketone; vinyl isobutyl ether; vinyl ethyl ether; compounds that have a plurality of ethylenic bonds such as those having conjugated double bonds such as butadiene, 2 chlorobutadiene, isoprene; and the like. Examples of preferable acrylates and methacrylates are disclosed in Skoultchi, U.S. Pat. No. 5,286,821 at column 3, lines 50 to column 6, line 12, incorporated herein by reference and Pocius, U.S. Pat. No. 5,681,910 at column 9, line 28 to column 12, line 25, incorporated herein by reference. More preferred olefinic compounds comprise methyl acrylate, methylmethacrylate, butylmethacrylate, tert-butylmethacrylate, 2-ethylhexyacrylate, 2-ethylhexylmethacrylate, ethylacrylate, isobornylmethacrylate, isobornylacrylate, hydroxyethylmethacrylate, glycidylmethacrylate, tetrahydrofurfuryl methacrylate, acrylamide, n-methylacrylamide, and other similar acrylate containing monomers. Also useful are the class of acrylate tipped polyurethane prepolymers available commercially from several sources, and prepared by reacting an isocyanate reactive acrylate monomer, oligomer or polymer, such as a hydroxy acrylate, with an isocyanate functional prepolymer.

In the embodiment where the composition is used as an adhesive, acrylate and/or methacrylate based compounds are preferably used. The most preferred acrylate and methacrylate compounds include methylmethacrylate, butylmethacrylate, 2-ethylhexylmethacrylate, isobornylmethacrylate, tetrahydrofurfuryl methacrylate, and cyclohexylmethylmethacrylate.

In some embodiments the polymerizable compositions of the invention may further comprise an effective amount of a compound that is reactive with an amine so as to liberate the organoborane so as to initiate polymerization (a decomplexing agent). The amine reactive compound liberates organoborane by reacting with the amine, thereby removing the organoborane from chemical attachment with the amine. Desirable amine reactive compounds are those materials that can readily form reaction products with amines at or below and more preferably at room temperature, about 20° C. to 22° C., so as to provide a composition that can be generally easily used and cured under ambient conditions. General classes of such compounds include acids, aldehydes, isocyanates, acid chlorides, sulphonyl chlorides, mixtures thereof and the like. Preferred amine reactive compounds are acids. Both Bronstead and Lewis acids may be used. Pocius, U.S. Pat. No. 5,718,977 describes the preferred acid compounds at column 9, line 1 to 15 incorporated herein by reference. The most preferred acids are acrylic acid and methacrylic acid.

Preferably the amount of polymerizable compounds in the polymerizable compositions or adhesive is about 20 percent by weight or greater based on the weight of the total composition, more preferably about 30 percent by weight or greater and most preferably about 40 percent by weight or greater. Preferably the amount of polymerizable compounds is about 95 percent by weight or less, preferably about 90 percent by weight or less and most preferably about 85 percent by weight or less. The amount of complex used in the composition can be any amount sufficient to initiate polymerization once the complex has disassociated at the desired speed of polymerization. At higher concentration of organoborane, the speed of polymerization is higher. Preferably the amount of organoborane complex is about 0.2 percent by weight or greater based on the weight of the total composition, preferably about 1.0 percent by weight or greater and most preferably about 2 percent by weight or greater. Preferably the amount of organoborane complex present is about 8 percent by weight or less based on the total weight of composition, preferably about 6 percent by weight or less and most preferably about 4 percent by weight or less. In those embodiments where a decomplexing agent is used, the amount of decomplexing agent (initiator) is that amount which is sufficient to initiate disassociation of the organoborane-amine complex thereby causing the organoborane to initiate polymerization of the olefinically unsaturated compound. Preferably the amount of decomplexing agent is about 1 percent by weight or greater based on the weight of the total composition, more preferably about 1.5 percent by weight or greater and most preferably about 2.0 percent by weight or greater. Preferably the amount of decomplexing agent is about 8 percent by weight or less based on the weight of the total composition, more preferably about 6 percent by weight or less and most preferably about 4 percent by weight or less.

The organoborane amine complex may be readily prepared using known techniques. Typically, the amine is combined with the organoborane in an inert atmosphere with slow stirring. An exotherm is often observed and cooling of the mixture is, therefore, recommended. If the ingredients have a high vapor pressure, it is desirable to keep the reaction temperature below about 70° C. to 80° C. Once the materials are well mixed the complex is permitted to cool to room temperature. No special storage conditions are required although it is preferred that the complex be kept in a capped vessel under an inert atmosphere, in a cool, dark location. Advantageously, the complexes of the invention can be prepared in the absence of organic solvents that would later have to be removed, although they could be prepared in solvent, if so desired. Solvents used in the preparation of the complexes should, preferably, be ones that do not coordinate the amine, preferable solvents are for example, tetrahydrofuran or diethylether, or low molecular weight alkanes such as hexane or heptane.

The complexes and compositions of the invention are air stable. By "air stable" it is meant that when the complexes are stored in a capped vessel at room temperature (about 20° C. to 22° C.) and under otherwise ambient conditions (i.e., not under a vacuum and not in an inert atmosphere), the complexes remain useful as polymerization initiators for at least about two weeks, although the complexes may be readily stored under these conditions for many months.

By "air stable" it is also meant that the complexes are not pyrophoric. (When a few drops of the complex are placed on a paper towel under ambient conditions, the paper towel does not ignite, char or smoke.) The air stability of the complex is enhanced when the complex is a crystalline material. However, the complexes of the invention are air stable for at least six months even when they are liquids. Liquid complexes are easier to handle and mix than are crystalline complexes.

The polymerizable compositions of the invention can be either one or two-part compositions depending upon the mechanism used to initiate polymerizations. In one embodiment the compositions are two-part compositions in which one-part contains the complexes of the invention and the other part contains the decomplexing agent (initiator). Polymerization is initiated by contacting the two-parts of the composition. An advantage of this process is that polymerization can be initiated at, or even below, ambient temperatures. In this embodiment heat may be applied to the polymerizable composition to speed up initiation or polymerization. In another embodiment the polymerization composition may be initiated by heating the composition. In this embodiment no decomplexing agent (initiator) is needed.

When polymerization is initiated by heating the composition can be either a one-part or a two-part composition. The primary reason to use a two-part composition is to keep apart components of the composition which may be unstable in the presence of one another.

In the embodiment where heat is used to initiate the cure of the composition, the composition is exposed to a heat source which heats the composition to a temperature at or above the temperature at which the complex used in the composition decomposes to release the organoborane which then initiates free radical polymerization. Generally the composition is heated to a temperature which is less than the temperature at which the polymer formed undergoes degradation. The temperature at which the complex undergoes disassociation is related to the binding energy of the complex. At higher binding energies of the complex higher temperatures are required to initiate polymerization. In the embodiment where the polymerization is initiated thermally the temperature at which the composition is heated to initiate polymerization is dictated by the binding energy of the complex. Generally the temperature used to initiate the polymerization by decomplexing the complex is about 30° C. or greater and preferably about 50° C. or greater. Preferably the temperature at which thermally initiated polymerization is initiated is about 120° C. or less and more preferably about 100° C. or less. Any heat source which heats the composition to the desired temperature can be used provided the heat source does not negatively impact the components of the composition or its function. In this manner the composition may be contacted with the substrates either before or after the composition is exposed to heat. If the composition is heated prior to contact with the substrates, the composition should be contacted with the substrates before the composition has polymerized to the point at which the composition is no longer able to adhere to the substrates, this is usually the upper limit on the open time as defined hereinafter. It may be necessary in the thermally initiated reaction to control the oxygen content such that there is adequate oxygen to create favorable conditions for radical formation but not so much as to inhibit the polymerization.

The two-part polymerizable compositions or adhesive compositions of the invention are uniquely suited for use with conventional, commercially available dispensing equipment for two-part adhesives. Once the two-parts have been combined, the composition should be used quickly, as the useful pot life (or open time) may be short depending upon the monomer mix, the amount of complex, and the temperature at which the bonding is to be performed. The adhesive composition is applied to one or both substrates and then the substrates are joined together with pressure to force excess composition out of the bond line. This also has the advantage of displacing composition that has been exposed to air and that may have begun to react. In general, the bonds should be made shortly after the composition has been applied, preferably within about 10 minutes. The typical bond line thickness is about 0.005 inches (0.13 mm) to about 0.03 inches (0.76 mm). The bonding process can easily be carried out at room temperature and to improve the degree of polymerization it is desirable to keep the temperature below about 40° C., preferably below about 30° C., and most preferably below about 25° C.

The bonds will cure to a reasonable green strength to permit handling of the bonded components within about 2 to 3 hours. Full strength will be reached in about 24 hours under ambient conditions; post-curing with heat (typically about 80° C.) may be used if desired.

When bonding fluoroplastics, it is advantageous to cool the initiator containing part of the two-part composition to about 0° C. to about 5° C. before adding the organoborane amine complex. The bond should be made as soon after the composition has been applied as practical; performing the bonding operation at less than about room temperature is also helpful.

The compositions may further comprise a variety of optional additives. One particularly useful additive is a thickener such as medium to high (about 10,000 to about 1,000,000) molecular weight polymethyl methacrylate which may be incorporated in an amount of about 10 to about 60 weight percent, based on the total weight of the composition. Thickeners may be employed to increase the viscosity of the composition to facilitate application of the composition.

Another particularly useful additive is an elastomeric material. The materials can improve the fracture toughness of compositions made therewith which can be beneficial when, for example, bonding stiff, high yield strength materials such as metal substrates that do not mechanically absorb energy as easily as other materials, such as flexible polymeric substrates. Such additives can be incorporated in an amount of about 5 percent to about 35 percent by weight, based on the total weight of the composition. Useful elastomeric modifiers include chlorinated or chlorosulphonated polyethylenes such as HYPALON 30 (commercially available from E. I. Dupont de Nemours & Co., Wilmington, Del.) and block copolymers of styrene and conjugated dienes (commercially available from Dexco Polymers under the Trademark VECTOR, and Firestone under the Trademark STEREON). Also useful, and even more preferred, are certain graft copolymer resins such as particles that comprise rubber or rubber-like cores or networks that are surrounded by relatively hard shells, these materials often being referred to as "core-shell" polymers. Most preferred are the acrylonitrile-butadiene-styrene graft copolymers available from Rohm and Haas. In addition to improving the fracture toughness of the composition, core-shell polymers can also impart enhanced spreading and flow properties to the uncured composition. These enhanced properties may be manifested by a reduced tendency for the composition to leave an undesirable "string" upon dispensing from a syringe-type applicator, or sag or slump after having been applied to a vertical surface. Use of more than about 20% percent of a core-shell polymer additive is desirable for achieving improved sag-slump resistance. Generally the amount of toughening polymer used is that amount which gives the desired toughness to the polymer or the adhesive prepared.

Another useful adjuvant is a cross-linking agent. Cross-linking agents can be used to enhance the solvent resistance of the adhesive bond or polymer composition, although certain compositions of the invention have good solvent resistance even in the absence of externally added cross-linking agents. Typically employed in an amount of about 0.2 to about 10 weight percent based on the total weight of the compositions, useful cross-linkers include the various diacrylates referred to above as possible acrylic modifying monomers as well as other materials. Particular examples of suitable cross-linking agents include ethylene glycol dimethacrylate, ethylene glycol diacrylate, triethyleneglycol dimethacrylate, diethylene glycol bismethacryloxy carbonate, polyethylene glycol diacrylate, tetraethylene glycol dimethacrylate, diglycerol diacrylate, diethylene glycol dimethacrylate, pentaerythritol triacrylate, trimethylolpropane triglycidyl ether, trimethylolpropane tris(2-methyl-1- aziridinepropionate, trimethylolpropane trimethacrylate, acrylate tipped polyurethane containing prepolymers, polyether diacrylates and dimethacrylates.

Peroxides may be optionally included (typically in an amount of about 2 percent by weight or less, based on the total weight of the composition), for example, to adjust the speed at which the compositions polymerize or to complete the polymerization.

Small amounts of inhibitors such as hydroquinone may be used, for example, to prevent or reduce degradation of the olefinic monomers during storage. Inhibitors may be added in an amount that does not materially reduce the rate of polymerization or the ultimate properties of an adhesive or other composition made therewith, typically about 10 to about 10,000 ppm based on the weight of the polymerizable monomers.

Other possible additives include non-reactive colorants, fillers (e.g., carbon black), etc.

The various optional additives are employed in an amount that does not significantly adversely affect the polymerization process or the desired properties of compositions made therewith.

Polymerizable compositions according to the invention may be used in wide variety of ways, including as sealants, coatings, primers, to modify the surface of polymers, and injection molding resins. They may also be used as matrix resins in conjunction with glass and metal fiber mats such as in resin transfer molding operations. They may further be used as encapsulants and potting compounds such as in the manufacture of electrical components, printed circuit boards and the like. Quite desirably, they provide polymerizable adhesive compositions that can bond a diverse myriad of substrates, including polymers, wood, ceramics, concrete, glass and primed metals. Another desirable related application is their use in promoting adhesion of paints to low surface energy substrates such as polyethylene, polypropylene, polyethyleneterephthalate and polytetrafluoroethylene, and their co-polymers. In this embodiment the composition is coated onto the surface of the substrate to modify the surface to enhance the adhesion of the final coating to the surface of the substrate.

The compositions of the invention can be used in coating applications. In such applications the composition may further comprise a carrier such as water or a solvent. The coating may further contain additives well known to those skilled in the art for use coatings such as pigments to color the coating, inhibitors and UV stabilizers. The compositions may also be applied as powder coatings and may contain the additives well known to those skilled in the art for use in powder coatings.

The compositions of the invention can also be used to modify the surface of a polymeric molded part, extruded film or contoured object. Compositions of the invention can also be used to change the functionality of a polymer particle by surface grafting of polymer chains on to the umnodified plastic substrate.

Alternatively, the complexes of the present invention can be dissolved in a variety of solvents including water or organic solvents that provide a non acid containing environment and used as a primer. In this manner the complex containing solution is applied to the surface that is to be used for adhesion, surface modification, or polymerization, and the solvent allowed to dry. The polymerizable monomer is then brought into contact with the complex on the surface and allowed to react for the purpose of promoting adhesion, or surface modification, or for initiating radical polymerization Polymerizable compositions of the invention are especially useful for adhesively bonding low surface energy plastic or polymeric substrates that historically have been very difficult to bond without using complicated surface preparation techniques, priming, etc. By low surface energy substrates is meant materials that have a surface energy of about 45 $mJ/m^2$ or less, more preferably about 40 $mJ/m^2$ or less and most preferably about 35 $mJ/m^2$ or less. Included among such materials are polyethylene, polypropylene, acrylonitrile-butadiene-styrene, polyamides, syndiotactic polystyrene, olefin containing block co-polymers, and fluorinated polymers such as polytetrafluoroethylene (TEFLON) which has a surface energy of less than about 20 $mJ/m^2$. (The expression "surface energy" is often used synonymously with "critical wetting tension" by others.) Other polymers of somewhat higher surface energy that may be usefully bonded with the compositions of the invention include polycarbonate, polymethlmethacrylate, and polyvinylchloride.

The polymerizable compositions of the invention can be easily used as two-part adhesive. The components of the polymerizable compositions are blended as would normally be done when working with such materials. The decomplexing agent is usually included in this blend so as to separate it from the organoborane amine complex, thus providing one-part of the two-part composition. The organoborane amine complex of the polymerization initiator system provides the second part of the composition and is added to the first part shortly before it is desired to use the composition. The complex may be added to the first part directly or it may be pre-dissolved in an appropriate carrier such as methyl methacrylate.

It may be desirable to store the complexes apart from the monomers, oligomers or polymers to inhibit premature polymerization of the monomers, oligomers or polymers. The complexes of this invention have greatly enhanced stability when in the presence of monomers and in the absence of a decomplexing agent, such as an acid, and thus can be stored with the polymerizable components of the composition. Complexes in which the complexing amine nitrogen atom to boron atom ratio is greater than 1:1 may be sufficiently stable that they can be blended with polymerizable components in useful proportions. However, in such situations, the presence of additional non-polymerizing reactants (e.g., the organoborane liberator) may result in other, undesirable affects.

For a two-part adhesive such as those of the invention to be most easily used in commercial and industrial environments, the ratio at which the two-parts are combined should be a convenient whole number. This facilitates application of the adhesive with conventional, commercially available dispensers. Such dispensers are shown in U.S. Pat. Nos. 4,538,920 and 5,082,147 (incorporated herein by reference) and are available from Conprotec, Inc. (Salem N.J.) under the trade name MIXPAC. Typically, these dispensers use a pair of tubular receptacles arranged side-by-side with each tube being intended to receive one of the two-parts of the adhesive. Two plungers, one for each tube, are simultaneously advanced (e.g., manually or by a hand-actuated ratcheting mechanism) to evacuate the contents of the tubes into a common, hollow, elongated mixing chamber that may also contain a static mixer to facilitate blending of the two-parts. The blended adhesive is extruded from the mixing chamber onto a substrate. Once the tubes have been emptied, they can be replaced with fresh tubes and the application process continued.

The ratio at which the two-parts of the adhesive are combined is controlled by the diameter of the tubes. (Each plunger is sized to be received within a tube of fixed diameter, and the plungers are advanced into the tubes at the same speed.) A single dispenser is often intended for use with a variety of different two-part adhesives and the plungers are sized to deliver the two-parts of the adhesive at a convenient mix ratio. Some common mix ratios are 1:1, 2:1, 4:1 and 10:1.

The part of the adhesive or polymerizable compositions of the invention which contain the amine-organoborane complex preferably displays thermal stability at, or above, room temperature. Thermal stability as used herein means the amine organoborane complex does not disassociate and initiate polymerization of the olefinic unsaturated compounds present in the composition. Thermal stability can be measured by determining the temperature at which the viscosity of the composition begins to increase. Preferably the temperature at which the viscosity of the composition increases is greater than about 40° C., more preferably greater than about 60° C. and most preferably greater than about 80° C. The increase in viscosity indicates that the amine borane complex is disassociated and polymerization has been initiated. In the embodiment wherein the composition is used as an adhesive, the adhesive preferably demonstrates a lap shear strength of about 100 p.s.i. (689 kPa) or greater, more preferably about 250 p.s.i. (1724 kPa) or greater and more preferably about 400 p.s.i. (2758 kPa) or greater according to the following test procedure.

The adhesive components are mixed and applied to one or both substrates (1 in×4 in×⅛ in (25.4 mm×101.6 mm×3.2 mm) polypropylene coupons). Adhesive thickness can be controlled by the addition of a few weight percent of glass beads between 0.005 to 0.030 inches in diameter (0.13 mm to 0.76 mm). The coupons are mated to provide 0.5 inch squared (161 mm$^2$) to 1.0 inch squared (645 mm$^2$) substrate overlap in a lap-shear testing configuration. The samples are held in place with metal binder clips to provide constant force and facilitate the elimination of air bubbles in the adhesive. The bonded samples were usually cured for at least about 24 hours before being mounted in a tensile testing apparatus fitted with a sample oven. The samples are evaluated at crosshead speeds of 0.05 (0.13 mm) and 0.5 (12.7 mm) inches per minute for room temperature and 110° C. testing conditions, respectively. Maximum load (pounds) to break are recorded and maximum stress (psi) is calculated by dividing this load by the overlap area (inches squared).

Preferably the open time of the adhesive is about 3 minutes or greater, more preferably about 5 minutes or greater, and most preferably about 8 minutes or greater. Preferably the open time of the adhesive is about 30 minutes or less, more preferably about 25 minutes or less, and most preferably about 20 minutes or less. Open time as used herein is the time between initiation of polymerization and the time at which the adhesive can no longer be applied and used as an adhesive. If the open time is too long, poor bond strength is observed. If the open time is too short, the composition polymerizes before a link up with the substrate can be achieved.

Preferably the polymeric compositions of the invention have a suitable viscosity to allow application. Preferably the compositions have the viscosity of about 100 centipoise or greater, more preferable about 1,000 centipoise or greater and most about 20,000 centipoise or greater. Preferably the adhesive compositions have a viscosity of about 150,000 centipoise or less, more preferably about 100,000 centipoise or less and most preferably about 50,000 centipoise or less.

Specific Embodiments

The following examples are included for illustrative purposes only and are not intended to limit the scope of the claims. Unless otherwise stated all parts and percentages are by weight.

Preparation of the Organoborane/Amine Complex 50 cc of a 1M solution of organoborane, for example tributyl borane (TBB) in ether solution (Aldrich), is added to a weighed round bottom flask. The solution is purged with nitrogen. A weighed amount of the amine, for example pyrrolidine (4.97 g, 1:1.4 molar ratio of boron to amine), is added in small portions to the organoborane solution, maintaining the temperature below 40° C. with an external ice bath. The amine is added to make a molar ratio of organoborane to amine of between 1:1 to a 1:3. The solution is stirred for about 30 minutes and then the solvent is removed on a rotary evaporator at less than 40° C. The weight of the flask and complex are periodically compared to the theoretical weight to assure that the solvent is completely removed. The complex is tested for pyrophoric reactivity by placing a drop on a paper towel and looking for charring of the towel. Some pyrophoric complexes can be made less or non-pyrophoric by adding additional amine (lowering the organoborane:amine molar ratio).

Preparation of Adhesive Compositions

Two component (part) adhesives are produced as described below. One component includes the organoborane/amine complex (hardener) mixed with an acrylic resin, described below, and an antioxidant. The other component is the acrylic resin with an initiator, for example acrylic acid, that decomplexes the boron/amine complex when mixed into the other component. The acrylic resin is a mixture of 250 g methylmethacrylate (MMA) and 80 g polymethylmethacrylate (PMMA, 350 K Mw). The MMA and PMMA are stirred or rotated overnight to mix the PMMA into the MMA. The resulting acrylic resin has with a viscosity of about 25,000 centipoise (cP).

The first component (Part I) comprises 135 g acrylic resin, 6.6 g of a hardener, and 82.5 mg BHT (2,6-ditertbutyl-4-methyl phenol). The second component comprises 135 g acrylic resin, 6.6 g acrylic acid (AA), 13.5 g fillers (glass beads, polypropylene ground flakes, etc.) (<10%), and 13.5 g tougheners (Stereon 840A block copolymer) (<10%)). The two components of the adhesive composition are formulated to allow for a ratio of 1:1, 1:4, or 1:10 mixture of hardener:initiator, preferably 1:1.

The adhesive may be mixed in the desired ratio in air, in a bag, or through a pressurized gun. The adhesive is applied to a polypropylene test strip 1 inch (25.4 mm) wide with a ½ inch (12.7 mm) overlap and is tested for adhesive strength as described previously.

Thermal stability testing is performed according to the procedures provided below. The auto-initiation temperature is determined from the point at which the viscosity starts to rise, indicating the onset of polymerization of the borane:amine containing resin without initiator. Onset occurs due to thermal destabilization of the boron/amine complex. Viscosity is measured continuously by a Brookfield viscometer (rotating cylinder at 50 rpm) as a function of a constant temperature ramp (about 1° C./min). The temperature at which the viscosity begins to increase is noted and listed as the take off temperature.

In another method the time it takes for the viscosity to reach 100 kcPs at ambient temperature (or elevated temperature) is determined by periodic measurement of the viscosity of a hardener and resin over a period of days. This is considered to be the useful lifetime of the resin.

Several complexes were prepared and tested in the composition as described herein. Table 1 contains the results of the testing.

The following abbreviations are used in Table 1.

TBB is tri-n-butyl borane.

DMAPA is dimethylaminopropylamine.
TiBB is triisobutylborane.
DEBM is diethylmethoxyborane
DEBI is diethylisopropoxy borane
TOB is tri-n-octylborane
> means the substrate broke during measurement Y means that paper ignited or charred when contacted with the borane:amine
N means that paper did not ignite, char, smoke, or discolor when contacted by borane:amine.
Sl means that the paper showed slight evolution of smoke or discoloration, but not charring when contacted with borane:amine.

TABLE 1

| Example | Borane | Amine | Molar B:Amine | Pyro-phoric? | Take-off Temp (C.) | Lap Shear (on PP) psi |
|---|---|---|---|---|---|---|
| 1 | TBB | Hexane diamine | 1:1 | N | 44 | >444 |
| 2 | TBB | DMAPA | 1:1.1 | N | 52 | >900 |
| 3 | TBB | DMAPA | 1:1.2 | N | 53 | >655 |
| 4 | TiBB | DMAPA | 1:1.25 | N | 39 | >604 |
| 5 | TBB | DMAPA | 1:0.6 | N | 47 | >929 |
| 6 | TBB | Tetramethyl propane diamine | 1:3 | Y | 46 | 192 |
| 7 | TPB | DMAPA | 1:1.1 | N | >100 | 0 |
| 8 | TBB | Aminopropyl morpholine | 1:1.1 | N | 50 | >682 |
| 9 | TBB | Cyclohexylamine | 1:1.2 | sl | 20 | >933 |
| 10 | TBB | Aminopropanol | 1:1.2 | N | 20 | >624 |
| 11 | TBB | Morpholine | 1:1.2 | Y | 20 | >818 |
| 12 | TBB | Ethanolamine | 1:1.17 | N | 42 | 458 |
| 13 | TBB | Piperidine | 1:1.5 | N | 52 | >783 |
| 14 | TBB | Pyrrolidine | 1:1.4 | N | >100 | 679 |
| 15 | DEBM | DMAPA | 1:1.25 | N | 68 | 36 |
| 16 | DEBI | DMAPA | 1:1.25 | N | 77 | 64 |
| 17 | TBB | Isophorone diamine | 1:1.36 | N | 46 | >893 |
| 18 | TBB | Methoxypropyl amine | 1:1.36 | N | 63 | >640 |
| 19 | TBB | a-Methyl Benzylamine | 1:1.6 | sl | 25 | 451 |
| 20 | TOB | DMAPA | 1:1.3 | N | >100 | 471 |
| 21 | TBB | Aminopropyl propane diamine | 1:1.2 | N | 64 | >559 |
| 22 | TBB | Aminoethoxy ethanol | 1:1.3 | N | 25 | >847 |
| 23 | TOB | Methoxypropyl amine | 1:1.3 | N | 68 | 110 |
| 24 | TOB | Aminopropanol | 1:1.3 | N | 53 | 79 |
| 25 | TBB | Morpholine | 1:3 | N | 42 | >878 |
| 26 | TBB | Aminopropanol | 1:2 | N | 60 | >419 |
| 27 | TOB | Isophorone diamine | 1:1.3 | N | >100 | 0 |
| 28 | TBB | Diisopropyl amine | 1:2 | Y | 50 | 0 |
| 29 | TBB | Cyclohexylamine | 1:2 | N | 30 | 508 |
| 30 | TBB | Piperidine | 1:2 | N | 85 | >775 |
| 31 | TBB | Aminoethoxy ethanol | 1:2 | N | 50 | 276 |
| 32 | TBB | Pyrrolidine | 1:1.4 | N | >100 | >709 |
| 33 | TiBB | Pyrrolidine | 1:1.4 | N | >100 | 303 |
| 34 | TBB | Piperazine | 1:1.3 | N | 20 | >749 |
| 35 | TBB | Methyl pyrrolidinone | 1:2 | Y | 20 | 0 |
| 36 | TBB | Tetrahydro-thiophene | 1:1.3 | N | 20 | 0 |
| 37 | TBB | Diethanol amine | 1:2 | Y | 65 | 61 |
| 38 | TBB | Triethyl amine | 1:2 | Y | 52 | 0 |
| 39 | TBB | Dibutylamine | 1:1.3 | N | 50 | 39 |
| 40 | TBB | Dipropylamine | 1:1.3 | Y | 52 | 0 |
| 41 | TBB | Dioctylamine | 1:1.3 | N | 58 | 192 |
| 42 | TBB | Cyclopentyl amine | 1:1.3 | Y | 25 | >790 |
| 43 | TBB | Cyclopentyl amine | 1:2 | N | 25 | >940 |
| 44 | TiBB | Isophorone diamine | 1:1.3 | N | 25 | 300 |
| 45 | TOB | Methoxypropyl amine | 1:1.3 | N | 50/83 | |
| 46 | TBB | 1,3,3 trimethyl 6-aza bicyclo [3,2,1] octane | 1:1.3 | N | 25/>100 | >426 |
| 47 | TBB | Dabco | 1:1.3 | sl | 25 | >774 |

TABLE 1-continued

| Example | Borane | Amine | Molar B:Amine | Pyrophoric? | Take-off Temp (C.) | Lap Shear (on PP) psi |
|---|---|---|---|---|---|---|
| 48 | TBB | Diamino maleonitrile | 1:1.3 | Y | | NA |
| 49 | TBB | Thiazolidine | 1:1.3 | Y | 25 | >725 |
| 50 | TBB | Thiazolidine | 1:2 | N | 25 | 186 |
| 51 | TBB | Urea | 1:1.3 | Y | | NA |
| 52 | TBB | 1,8 Diaza bicyclo[5,4]undec-7-ene | 1:1.3 | N | >100 | >555 |
| 53 | TBB | 4-Dimethylamino pyridine | 1:3 | N | 57 | >581 |
| 54 | TBB | Praline methyl ester | 1:1.3 | N | | 0 |
| 55 | TBB | 4-Bromo piperidine | 1:1.3 | Y | | 0 |
| 56 | TBB | Acetaldehyde Ammonia Trimer | 1:1.3 | sl | 67 | 0 |
| 57 | TBB | 1-Amino-4-Methyl Piperazine | 1:1.3 | N | 25 | 145 |
| 58 | TBB | Homopiperazine | 1:1.3 | N | 25 | 638 |
| 59 | TBB | 2-Dimethylaminopyridine | 1:3 | sl | 25 | 0 |
| 60 | TBB | Pyridine | 1:3 | N | 25 | |
| 61 | TBB | Tetraaza adamantane | 1:2 | Y | | 0 |
| 62 | TBB | Hexylamine | 1:1.3 | N | 45 | >885 |
| 63 | TBB | Tetramethylguanidine | 1:1.3 | N | 74 | >616 |
| 64 | TBB | Tetrahydropyrimidine | 1:1.3 | N | 75 | >736 |
| 65 | TBB | 2-Methyl 2-imidazoline | 1:1.3 | N | 35 | >1000 |
| 66 | TBB | 3-Pyrroline | 1:1.3 | N | 25 | 247 |
| 67 | TBB | Trimethylolpropane tris[poly(propyleneglycol), amine terminated] ether (avg mwt = 432) | 1:1.3 | N | 42 | >620 |
| 68 | TBB | Trimethylolpropane tris (2-methyl-1-aziridinepropionate | 1:1.3 | Y | <25 | 0 |

Binding Energies of Complexes

The organoborane/amine binding energies of several of the complexes are calculated using previously described computational methods. Comparison of results of amine/organoborane combinations listed in Table 1 with calculated binding energies in Table 2 reveal that binding energies less than about 10 kcal/mole are pyrophoric, and a high binding energy is correlated with higher thermal performance. Furthermore the calculated binding energy is correlated with the temperature at which the alkylborane-amine complex spontaneously disassociates. The disassociation temperature is easily determined by the so called "take-off" temperature provided in Table 1 at which time the polymerization proceeds in the absence of a de-complexing agent. The disassociation temperature may also be determined by differential scanning calorimetry. When applying differential scanning calorimetry, a sample of the complex is placed in a pan and the temperature of the pan is raised. At the same time a reference sample, usually an empty pan, is heated at the exact same rate and the difference in temperature between the sample and the reference is monitored and recorded using a differential amplifier. When reaction of the complex is observed an exotherm can be observed implying a release of heat due to insertion of oxygen into the alkyl-boron bond. No exotherm is observed when this experiment is performed under strictly inert conditions.

TABLE 2

| Example | Lewis Acid | Amine | Binding Energy (kcal/mole) |
|---|---|---|---|
| 2 | TBB | DMAPA cyclic[1] | 20.4 |
| 2 | TBB | DMAPA linear | 15.9 |
| 25 | TBB | morpholine | 12.8 |
| 32 | TBB | pyrrolidine | 15.4 |
| 17 | TBB | isophorone diamine cis | 15.1 |
| 17 | TBB | isophorone diamine trans | 15.3 |
| 18 | TBB | methoxypropylamine cyclic[1] | 20.1 |
| 18 | TBB | methoxypropylamine, linear | 15.4 |
| 21 | TBB | aminopropylpropanediamine | 18.3 |
| 38 | TBB | triethylamine | 0.0 |
| 47 | TBB | Dabco | 10.2 |
| 53 | TBB | 4-dimethylaminopyridine | 16.2 |
| 60 | TBB | pyridine | 8.7 |
| | TBB | dimethylaminoethylamine | 18.8 |
| | TBB | dimethylaminobutylamine | 21.9 |
| | TBB | propylamine | 15.8 |
| | TBB | acetamidine | 19.2 |
| | TBB | guanidine | 21.0 |
| | TBB | cyclopropeneimine | 17.0 |
| | TBB | tetramethyldiaminocyclopropene imine | 23 |
| | TBB | 3-N-methyl-3,4,5,6-tetrahydropyrimidine | 16.4 |
| | TBB | pyrazole | 10.2 |
| | TBB | 3-aminopyrazole | 13.1 |
| | TBB | aziridine | 18.0 |
| | TBB | methylaziridine | 14.9 |
| | TBB | azetidine | 17.9 |
| | TBB | methylazetidine | 12.2 |
| | TBB | formaldimine | 13.2 |
| | TBB | benzaldimine | 11.5 |

TABLE 2-continued

| Example | Lewis Acid | Amine | Binding Energy (kcal/mole) |
|---|---|---|---|
| | TBB | 3,4,5,6-tetrahydropyridine | 12.2 |
| | TBB | 5,6-dihydropyridine | 13.1 |
| | TBB | cyclohexanone imine | 12.8 |
| | TBB | 2-aminopropanal | 15.8 |
| | TBB | 1,4-dihydropyrrole | 15.0 |
| | TBB | N-Methyl-Tetrahydropyrimidine | 16.4 |
| | TBB | 1-azabutadiene | 13.8 |
| | TBB | 4-N,N-dimethylamino-1-azabutadiene | 19.5 |
| | TBB | 4-Methoxy-1-azabutadiene | 16.2 |
| | TBB | 4-Chloro-1-azabutadiene | 11.0 |
| | TBB | 1-Azahexatriene | 15.0 |

[1]Cyclic means two amines in the compounds associate electronically to form a quasi cyclic structure.

Among other compounds for which the binding energy is calculated, are those illustrated below with their calculated binding energies adjacent.

11.3

17.9

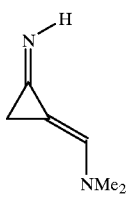

9.76

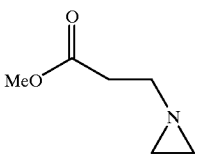

15.01

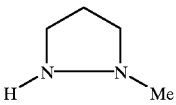

What is claimed is:

1. A method of priming the surface of a low surface energy polymer by contacting the surface with a composition comprising
    a) an organoborane/amine complex wherein the organoborane is a trialkyl borane or an alkyl cycloalkyl borane and the amine is selected from the group of amines having; comprising aliphatic heterocycles having at least one nitrogen in the heterocyclic ring wherein the heterocyclic compound may also contain one or more nitrogen atoms, oxygen atoms, sulfur atoms, or double bonds in the heterocycle; an alicyclic compound having bound to the ring a substituent having an amine moiety wherein the alicyclic compound may have a second substituent which can contain one or more nitrogen, oxygen or sulfur atoms and/or one or two double bonds; primary amines which in addition to a primary amine have one or more hydrogen bond accepting groups of an ether, polyether, thioether or halogen wherein there is an alkylene chain of at least two carbon atoms between the primary amine and the hydrogen bond accepting group, and conjugated imines;
    b) one or more of monomers, oligomers or polymers having olefinic unsaturation which is capable of polymerization by free radical polymerization;
    c) an effective amount of a compound which causes the complex to disassociate freeing the borane to initiate polymerization of the one or more monomers, oligomers or polymers having olefinic unsaturation; wherein the compound which causes disassociation of the complex is kept separate from the complex until initiation of polymerization is desired with at least a portion of the surface of the low surface energy polymer and causing the complex to disassociate thereby initiating polymerization of the monomer, oligomers, polymers or mixture thereof under conditions such that polymerization proceeds.

2. A method according to claim 1 wherein the complex of the organoborane and the primary amine corresponds to the formula

the organoborane heterocyclic amine complex corresponds to the formula

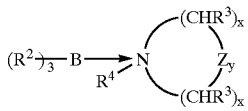

the organoborane conjugated imine complex corresponds to the formula

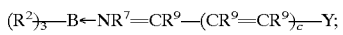

and an amine substituted alicyclic compound which corresponds to

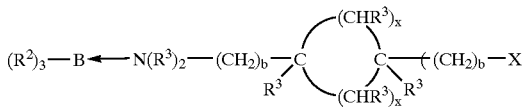

wherein

B is boron;

$R^1$ is separately in each occurrence hydrogen, a $C_{1-10}$ alkyl or $C_{3-10}$ cycloalkyl;

$R^2$ is separately in each occurrence a $C_{1-10}$ alkyl, $C_{3-10}$ cycloalkyl or two or more of $R^2$ may combine to form a cycloaliphatic ring structure;

$R^3$ is separately in each occurrence hydrogen, a $C_{1-10}$ alkyl $C_{3-10}$ cycloalkyl or forms a double bond with a $R^3$ or $R^4$ on an adjacent atom;

$R^4$ is separately in each occurrence hydrogen, $C_{1-10}$ alkyl, $C_{3-10}$ cycloalkyl, $C_{6-10}$ aryl or $C_{6-10}$ alkaryl;

$R^7$ is separately in each occurrence hydrogen, $C_{1-10}$ alkyl, or $C_{3-10}$ cycloalkyl;

$R^9$ is independently in each occurrence hydrogen, $C_{1-10}$ alkyl or $C_{3-10}$ cycloalkyl, Y,

or two or more of $R^9$ can combine to form a ring structure, or one or more of $R^9$ can form a ring structure with Y provided the ring structure is conjugated with respect to the double bond of the imine nitrogen;

$R^{9'}$ is independently in each occurrence hydrogen, $C_{1-10}$ alkyl, $C_{3-10}$ cycloalkyl or Y;

$R^{10}$ is separately in each occurrence $C_{1-10}$ alkyl, $C_{3-10}$ cycloalkyl or $—(C(R^1)_2)_d—W$;

W is separately in each occurrence hydrogen, $C_{1-10}$ alkyl or X;

X is $OR^{10}$, $SR^{10}$ or a halogen;

Y is independently in each occurrence hydrogen, $SR^4$, $OR^4$, $C(O)OR^4$, a halogen or an alkylene group which forms a cyclic ring with $R^7$ or $R^9$;

Z is separately in each occurrence oxygen or $—NR^4$;

a is separately in each occurrence an integer of from about 1 to about 10;

b is separately in each occurrence 0 or 1, with the proviso that the sum of a and b should be from about 2 to about 10;

c is separately in each occurrence an integer of from about 1 to about 10;

d is separately in each occurrence an integer of about 1 to about 4;

x is separately in each occurrence an integer of about 1 to about 10, with the proviso that the total of all occurrences of x is from about 2 to about 10; and y is separately in each occurrence 0 or 1.

3. A method according to claim 2 wherein:

$R^1$ is separately in each occurrence hydrogen or methyl;

$R^2$ is separately in each occurrence a $C_{2-4}$ alkyl group;

$R^3$ is separately in each occurrence hydrogen, methyl, or forms a double bond with an $R^3$ or $R^4$ on an adjacent atom;

$R^4$ is separately in each occurrence hydrogen, $C_{1-4}$ alkyl or;

$R^7$ is seperately in each occurrence hydrogen or methyl;

X is separately in each occurrence a $SR^{10}$ or $—OR^{10}$;

Y is separately in each occurrence $SR^4$, or $OR^4$, an alkylene group which can also form a cyclic ring with $R^7$ or $R^9$;

$R^9$ is separately in each occurrence hydrogen, a $C_{1-10}$ alkyl, Y,

or two or more of $R^9$ can form a cyclic ring one or more of $R^9$ or one or more of $R^9$ can combine with Y to form a ring structure;

$R^{9'}$ is independently in each occurrence hydrogen, $C_{1-10}$ alkyl or Y; and a is an integer of about 2 to about 6;

b is separately in each occurrence an integer of about 0 to about 1;

c is separately in each occurrence an integer of from about 1 to about 5; and d is separately in each occurrence an integer of about 2 to about 4.

4. A method according to claim 2 comprising an aliphatic heterocylic amine wherein the amine is a five or six membered heterocylic compound.

5. A method according to claim 2 wherein the amine is a conjugated imine.

6. A method according to claim 2 wherein the amine is an alicyclic compound having bound to the ring a substituent having an amine moiety wherein the alicyclic compound may have a second substituent which can contain one or more nitrogen, oxygen or sulfur atoms and/or one or two double bonds.

7. A method according to claim 6 wherein the alicyclic ring is a 5 or 6 membered ring.

8. A method according to claim 2 wherein the decomplexing agent is an acid.

9. A method according to claim 2 which comprises
   a) from about 0.2 to about 8 percent by weight of complex;
   b) from about 20 to about 95 percent by weight or less of monomers, oligomers or polymers;
   c) from about 1 to about 8 percent by weight of decomplexing agent; which further comprises
   d) from about 10 to about 60 percent by weight of a thickener; and
   e) from about 5 to about 35 percent by weight of an elastomeric material.

10. A method of priming the surface of a low energy polymer which comprises
    a) heating the components of the adhesive composition which comprises
       (i) an organoborane/amine complex wherein the organoborane is a trialkyl borane or an alkyl cycloalkyl borane and the amine is selected from the group of amines having an amidine structural component; aliphatic heterocycles having at least one nitrogen in the heterocyclic ring wherein the heterocyclic compound may also contain one or more nitrogen atoms, oxygen atoms, sulfur atoms, or double bonds in the heterocycle; an alicyclic compound having bound to the ring a substituent having an amine moiety wherein the alicyclic compound may have a second substituent which can contain one or more nitrogen, oxygen or sulfur atoms and/or one or two double bonds; primary amines which in addition to a primary amine have one or more hydrogen bond accepting groups of an ether, polyether, thioether or halogen wherein there is an alkylene chain of at least two carbon atoms between the primary amine and the hydrogen bond accepting group, and
       (ii) one or more of monomers, oligomers or polymers having olefinic unsaturation which is capable of polymerization by free radical polymerization to a temperature such that polymerization is initiated;
    b) contacting the composition with the surface of a low energy polymer; and
    c) allowing the composition to cure on the surface of the low energy polymer.

11. The method of claim 10 wherein the composition is heated to a temperature of about 40° C. or greater.

12. The method of claim 11 wherein the composition is heated to a temperature of about 50° C. to about 100° C.

13. A method according to claim 12 wherein the complex of the organoborane and the primary amine corresponds to the formula

the organoborane heterocyclic amine complex corresponds to the formula

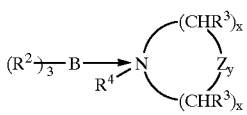

the organoborane amidine complex corresponds to the formula

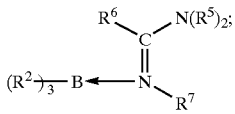

the organoborane conjugated imine complex corresponds to the formula

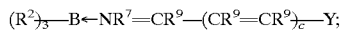

and the amine substituted alicyclic compound complex which corresponds to the formula

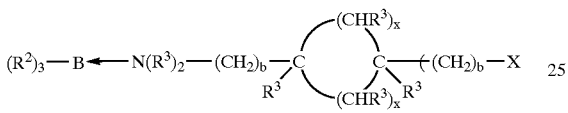

wherein

B is boron;

$R^1$ is separately in each occurrence hydrogen, a $C_{1-10}$ alkyl or $C_{3-10}$ cycloalkyl;

$R^2$ is separately in each occurrence a $C_{1-10}$ alkyl, $C_{3-10}$ cycloalkyl or two or more of $R^2$ may combine to form a cycloaliphatic ring structure;

$R^3$ is separately in each occurrence hydrogen, a $C_{1-10}$ alkyl $C_{3-10}$ cycloalkyl or forms a double bond with a $R^3$ or $R^4$ on an adjacent atom;

$R^4$ is separately in each occurrence hydrogen, $C_{1-10}$ alkyl, $C_{3-10}$ cycloalkyl, $C_{6-10}$ aryl or $C_{6-10}$ alkaryl;

$R^5$ and $R^6$ are separately in each occurrence hydrogen, $C_{1-10}$ alkyl, $C_{3-10}$ cycloalkyl, $N(R^4)_2$ wherein $R^7$ is separately in each occurrence hydrogen, $C_{1-10}$ alkyl, $C_{3-10}$ cycloalkyl or two or more of $R^5$, $R^6$ and $R^7$ in any combination can combine to form a ring structure which can be a single ring or a multiple ring structure and the ring structure can include one or more of nitrogen, oxygen or unsaturation in the ring structure;

$R^9$ is independently in each occurrence hydrogen, $C_{1-10}$ alkyl or $C_{3-10}$ cycloalkyl, Y,

or two or more of $R^9$ can combine to form a ring structure, or one or more of $R^9$ can form a ring structure with Y provided the ring structure is conjugated with respect to the double bond of the imine nitrogen;

$R^{9'}$ is independently in each occurrence hydrogen, $C_{1-10}$ alkyl, $C_{3-10}$ cycloalkyl or Y;

$R^{10}$ is separately in each occurrence $C_{1-10}$ alkyl, $C_{3-10}$ cycloalkyl or —$(C(R^1)_2)_d$—W;

W is separately in each occurrence hydrogen, $C_{1-10}$ alkyl or X;

X is $OR^{10}$, $SR^{10}$ or a halogen;

Y is independently in each occurrence hydrogen, $SR^4$, $N(R^4)_2$, $OR^4$, $C(O)OR^4$, a halogen or an alkylene group which forms a cyclic ring with $R^7$ or $R^9$;

Z is separately in each occurrence oxygen or —$NR^4$;

a is separately in each occurrence an integer of from about 1 to about 10;

b is separately in each occurrence 0 or 1, with the proviso that the sum of a and b should be from about 2 to about 10;

c is separately in each occurrence an integer of from about 1 to about 10;

d is separately in each occurrence an integer of about 1 to about 4;

x is separately in each occurrence an integer of about 1 to about 10, with the proviso that the total of all occurrences of x is from about 2 to about 10; and y is separately in each occurrence 0 or 1.

14. A method according to claim 13 wherein:

$R^1$ is separately in each occurrence hydrogen or methyl;

$R^2$ is separately in each occurrence a $C_{2-4}$ alkyl group;

$R^3$ is separately in each occurrence hydrogen, methyl, or forms a double bond with an $R^3$ or $R^4$ on an adjacent atom;

$R^4$ is separately in each occurrence hydrogen, $C_{1-4}$ alkyl or;

$R^5$ and $R^6$ are separately in each occurrence hydrogen, $C_{1-4}$ alkyl, $C_{5-6}$ cycloalkyl group, or $N(R^4)_2$, $R^7$ is separately in each occurrence hydrogen or methyl, with the proviso that two or more of $R^5$, $R^6$, and $R^7$ can combine in any combination to form a single or multiple ring structure and can include one or more of nitrogen, oxygen or unsaturation in the ring;

X is separately in each occurrence a $SR^{10}$ or —$OR^{10}$;

Y is separately in each occurrence $SR^4$, $N(R^4)_2$ or $OR^4$, an alkylene group which can also form a cyclic ring with $R^7$ or $R^9$;

$R^9$ is separately in each occurrence hydrogen, a $C_{1-10}$ alkyl, Y,

or two or more of $R^9$ can form a cyclic ring one or more of $R^9$ or one or more of $R^9$ can combine with Y to form a ring structure;

$R^{9'}$ is independently in each occurrence hydrogen, $C_{1-10}$alkyl, or Y; and a is an integer of about 2 to about 6;

b is separately in each occurrence an integer of about 0 to about 1;

c is separately in each occurrence an integer of from about 1 to about 5; and d is separately in each occurrence an integer of about 2 to about 4.

15. A method according to claim 13 comprising an aliphatic heterocyclic amine wherein the amine is a five or six membered heterocyclic compound.

16. A method according to claim 13 wherein the amine is a conjugated imine.

17. A method according to claim 13 wherein the amidine is a compound with an amidine structural component.

18. A method according to claim 13 wherein the amine is an alicyclic compound having bound to the ring a substituent having an amine moiety wherein the alicyclic compound may have a second substituent which can contain one or more nitrogen, oxygen or sulfur atoms and/or one or two double bonds.

19. A method according to claim 11 which comprises
a) from about 0.2 to about 8 to percent by weight of complex;
b) from about 20 to about 95 percent by weight or less of monomers, oligomers or polymers; which further comprises
c) from about 10 to about 60 percent by weight of a thickener; and
d) from about 5 to about 35 percent by weight of an elastomeric material.

* * * * *